United States Patent
Lurye

(10) Patent No.: US 11,642,383 B2
(45) Date of Patent: May 9, 2023

(54) METHOD OF SYNERGETIC MINIMIZATION OF NEGATIVE IMPACT CAUSED BY FLIGHTS ON HUMAN HEALTH

(71) Applicant: Arman Zhenisovich Lurye, Almaty (KZ)

(72) Inventor: Arman Zhenisovich Lurye, Almaty (KZ)

(*) Notice: Subject to any disclaimer, the term of this patent is extended or adjusted under 35 U.S.C. 154(b) by 318 days.

(21) Appl. No.: 16/983,829

(22) Filed: Aug. 3, 2020

(65) Prior Publication Data

US 2021/0220414 A1 Jul. 22, 2021

(30) Foreign Application Priority Data

Jan. 17, 2020 (KZ) .............................. 2020/0024.1

(51) Int. Cl.
| | | |
|---|---|---|
| *A61K 33/00* | (2006.01) | |
| *A61K 35/745* | (2015.01) | |
| *A61K 31/60* | (2006.01) | |
| *A61K 33/08* | (2006.01) | |
| *A61K 31/353* | (2006.01) | |
| *A61K 31/727* | (2006.01) | |
| *A61K 33/14* | (2006.01) | |
| *A61K 31/194* | (2006.01) | |
| *A61K 31/7004* | (2006.01) | |
| *A61K 33/30* | (2006.01) | |
| *A61K 31/695* | (2006.01) | |
| *A61K 31/454* | (2006.01) | |
| *A61K 31/5377* | (2006.01) | |
| *A61K 31/137* | (2006.01) | |
| *A61K 9/00* | (2006.01) | |
| *A61K 35/00* | (2006.01) | |

(52) U.S. Cl.
CPC .......... *A61K 35/745* (2013.01); *A61K 9/0053* (2013.01); *A61K 31/137* (2013.01); *A61K 31/194* (2013.01); *A61K 31/353* (2013.01); *A61K 31/454* (2013.01); *A61K 31/5377* (2013.01); *A61K 31/60* (2013.01); *A61K 31/695* (2013.01); *A61K 31/7004* (2013.01); *A61K 31/727* (2013.01); *A61K 33/08* (2013.01); *A61K 33/14* (2013.01); *A61K 33/30* (2013.01); *A61K 2035/115* (2013.01)

(58) Field of Classification Search
CPC .................................................... A61K 33/00
See application file for complete search history.

(56) References Cited

PUBLICATIONS

Berenbaum, "Syngergy, additivism and antagonism in immunosuppression," Clin Exp Immunol 28:1-18, 1977.*

Baker et al., "Optimal composition of fluid replacement beverages," Comprehensive Physiology 4:575-620, 2014.*
http://avia-life.com., internet source Oct. 1, 2019.
https://nv.ua/opinion/recommends/kak-na-samom-dele-vlijajut-na-nas-aviaperelety-1996883.html, internet source [retreived Oct. 1, 2019].
D.V. Sivukhin. General physics.—M.: Fizmatlit, 2005.—T.P. Thermodynamics and molecular physics—21-22 pages—544 pages—ISBN 5-9221-0601-5; http://moykonspekt.ru/fizika/izotermicheskij-process-zakon-bojlya-mariotta/.
Brief chemistry guide. Edition 4 (M, 1955, 113 pages); https://chem21.info/info/618833/.
S.A. Ivanova. General Practitioner https://bebeku.ru/menyaetsya-arterialnoe-davlenie-samolete/, internet source [retreived Oct. 1, 2019].
Maya Milich https://aif.ru/health/life/22241, internet source [retrieved Jan. 10, 2019].
I.N. Bokarev, L.V. Popova. Study of application of low molecular heparine for treatment of deep vein thrombosis (Russian) // Difficult patients—2008—V 6, issue 10.—42 pages—48.—ISSN 2074-1995.
Air flight. Harmful health risks and means of minimization. Recommendations of doctor Bitterlich https://www.dokbit.com/puteshestviya-sovety-vracha/aviaperelet/255-meditsinskaya-bezopasnost-pri-aviaperelete, internet source [retreived Oct. 1, 2019].
Plasma osmolarity—when is the indicator normal, what does it depend on, and how to calculate it? https://alkomir.net/ponyatie-osmolyarnosti-plazmy-krovi-ee-normy-i-prichiny-narusheniya-standartnyh-pokazatelej-osmolyarnost-krovi-ponyatie-normy-v-analizah-o-chem-govoryat-izmeneniya-znachenij/, internet source [retrieved Oct. 1, 2019].
Plasma osmolarity—when is the indicator normal, what does it depend on, and how to calculate it? https://alkomir.net/ponyatie-osmolyarnosti-plazmy-krovi-ee-normy-i-prichiny-narusheniya-standartnyh-pokazatelej-analiz-krovi-i-mochi-osmolyarnost/, internet source [retrieved Oct. 1, 2019].
Yu. V. Natochin. Electrolytic homeostasis and its clinical value // Russian journal of anaesthesiology and intensive therapy—1999.—No. 2.—33-52 pages (Abstract).

(Continued)

*Primary Examiner* — Rosanne Kosson
(74) *Attorney, Agent, or Firm* — The Roy Gross Law Firm, LLC; Roy Gross

(57) ABSTRACT

This invention is referred to the field of medicine, namely preventative treatment, and may be used as a means of synergetic minimization of negative impact of flights on human health (brain, stomach, lungs, blood vessels, heart etc.) with application of known substances and medicines with newly discovered pharmacological properties in new conditions. The ultimate technical solution of this invention would be synergetic minimization of negative impact of flying on human health without foot swelling, belching, jet-lag, tiredness and fatigue etc. The claimed technical result is achieved by the method of synergetic minimization of negative impact of air flights on human health, including consumption of substances that improve osmotic concentration of blood plasma, in the form of oral rehydration solution, split into two intakes as a minimum, first intake in the amount of at least 0.3 liters up to 1 liter before boarding and further during the flight from half an hour to 2 hours at least 0.3 liters to 1 liter and on as-needed basis.

9 Claims, No Drawings

(56) References Cited

PUBLICATIONS

W.J. Marshall. Clinical biochemistry—M.: Binom, SP: Nevsky dialect, 1999.—367 pages.
N.I. Gubanov and A.A. Utepbergenov. Medical biophysics, 149 pages, M, 1978.
Sodium chloride, https://medside.ru/natriya-hlorid, Internet source [retrieved Oct. 1, 2019].
Regidron, powder—https://health.mail.ru/drug/rehydron/, Internet source [retrieved Oct. 1, 2019].
Yana Alexandrovna Tsygankova, medical observer, GP, high qualification category. https://okeydoc.ru/espumizan-instrukciya-po-primeneniyu-pokazaniya-i-protivopokazaniya/, internet source [retrieved Oct. 1, 2019].
https://fb.ru/article/224899/mikroflora-kishechnika-vosstanovlenie-preparatyi-spisok-instruktsiya-po-primeneniyu-i-otzyivyi, internet source [retrieved Oct. 1, 2019].

* cited by examiner

METHOD OF SYNERGETIC MINIMIZATION OF NEGATIVE IMPACT CAUSED BY FLIGHTS ON HUMAN HEALTH

FIELD OF THE INVENTION

This application is a Non-Provisional Patent Application, which claims the benefit of priority from Kazakhstan Patent Application No. 2020/0024.1, filed Jan. 17, 2020. The contents of the above applications are all incorporated by reference as if fully set forth herein in their entirety.

BACKGROUND OF THE INVENTION

This invention is referred to the field of medicine, namely preventative treatment, and may be used as a means of synergetic minimization of negative impact of flights on human health (brain, stomach, lungs, blood vessels, heart etc.) with application of known substances and medicines with newly discovered pharmacological properties in new conditions.

LEVEL OF THE INVENTION

The doctors state that 10,000-meter altitude for humans, in a narrow airplane, is not a natural environment and could have a negative impact on health [1]. Human factor is often a cause of all airplane crashes.

Johann Hinkelbein, President of German Airspace Medicine Society, says that air travel has become cheap and popular and therefore this field raises huge interest among scientists and researchers. Hinkelbein, one of the scientists studying the impact of flying on human body and brain, emphasizes the following [2]:

- Decreased air pressure, like on 2.4 kilometer high mountain (about 550 mm Hg) results in minimized oxygen amount in passenger's blood by 6-25% (in such situations doctors in the hospital usually administer additional oxygen to the patient).
- Even relatively moderate levels of hypoxia (oxygen deficit) may change our ability to think clearly. Even healthy adults demonstrate changes in memory, computational and decision making abilities.
- Humidity level in the saloon is lower, than in some very dry deserts.
- But the scientist is sure that even moderate deficit level that we experience during the flights may have other, more recognizable effects—we get tired more easily.
- In addition to this, oxygen deficit may result in increased anxiety levels. Research studies demonstrate that at altitude we experience more negative thoughts, become more tense and less friendly and do not tend to deal with stress well.
- Hinkelbein discovered another change in the human body, namely, impact of flights on our immune system. It makes us more susceptible to various infections. [2].

As demonstrated by real flight data, some of significant harmful factors for passengers include the following:

1. Gas in confined spaces expands at altitude with pressure drop according to Boyle's (Boyle-Mariotte) law [3]. This results in ear, sinus pain, bloating and swelling in the stomach and pain in these organs.

2. Humans experience liquid loss in the form of evaporation through breathing and sweating at altitude with pressure drop. Air humidity in the airplane is very low, about 20-30%, which results in significant loss of liquid by the body and unpleasant symptoms—tickly throat, nose and mouth dryness, dry skin and eyes [3]. Sweating in the form of evaporation from the human body with atmospheric pressure drop will increase according to Dalton law [4], and may range from 200 ml to 800 ml per hour. Blood thickens under low pressure (at altitude) and huge water loss by the body. In response to these conditions (low pressure, oxygen deficit, increased blood viscosity) brain vessels spasm which results in poor blood flow in the brain with insufficient nutrient enrichment. There are unpleasant feelings with the following mechanisms: destroyed neuron communication between nerve cells, pathological changes in brain cells etc. Geodynamics in the legs gradually decreases and blood vessels narrow which results in increased blood pressure, labored breathing, rapid heartbeat, dizziness, fainting, irregular cardiac rhythm, increases stroke or heart attack risks [5].

Deep vein thrombosis which may develop when a passenger spends hours sitting presents a certain hazard for passenger life due to blood thickening [6].

In order to minimize risks may authors recommend to drink a lot of water, avoid caffeinated drinks (coffee, cola, etc.), do exercise, take anticoagulants, like warfarin or aspirin, have heparin injections [7].

"In order to minimize the risk of thrombosis and embolia passengers are recommended to take a medicine that minimizes blood clotting ability a day before the flight (one day before and then a few hours before the flight). The most common medicine is aspirin" [4, 8].

But none of the suggested measures and means (apart from minimized thrombosis hazard) provides a systematic solution of issues arising in the passenger body, starting from loss of liquid in the body due to irregular blood flow, belching and lowered immune system.

The objective of this invention is to eliminate the above shortages of equivalent medicine and comprehensive minimization of negative impact of flying on human health.

The ultimate technical solution of this invention would be synergetic minimization of negative impact of flying on human health without foot swelling, belching, jet-lag, tiredness and fatigue etc.

SUMMARY OF THE INVENTION

It was discovered that blood thinning will attribute to the solution of health-related issues arising in all human body systems. Osmotic concentration determines either blood thickness or thinness. Any deviations from the norm are signs of serious illnesses or pathological changes in the body [9]. Anticoagulants improve blood flow, but do not have any impact on blood thinning. Blood osmotic concentration (P) represents a total number of solid substances in plasma solution expresses in mOsm per 1 liter of water. Normal values are 297±2 mOsm/l. The osmotic concentration of blood plasma ranges from 280 to 300 mOsm/l. [10].

Irregular fluid balance or incorrect fluid transfer from the human body result in abnormal osmotic concentration of blood.

Main osmotic active cation in blood plasma is sodium. The osmotic concentration of plasma changes in parallel with its concentration. There is a close connection between the level of sodium and volume of circulated blood. Thus, increase in sodium concentration by 3 mmol/l above 145 is an indicator of loss of 1 l of water. Sodium concentration above 160 mmol/l certifies of water depletion in the body [11, 12].

The person feels thirsty in the event of decrease of water resources of the body or irregular water and minerals ratio (mainly sodium chloride). Replenishing human body with water maintains physiological level of fluid balance and electrolytic balance in the body [13].

Irregular fluid and electrolyte balance are expressed in the form of deficit or proficit of intercellular and intracellular water always associated with changes in electrolyte content. Electrolytes are a main support factor for high conductibility of electric impulses.

Significant deficit of electrolytes—desalination in the human body—takes place in cases when the loss of biological fluids that contain electrolytes is replenished with fresh water or glucose solution. This results in decreased osmotic concentration of intracellular fluid.

Sodium ions play a special role in maintenance of physiological values of osmotic pressure. Dehydration takes place as a result of changes in $Na^+$ ions. It is required to maintain electrolytic balance between intercellular and intracellular environments.

Pharmacopeia [14] states that sodium chloride maintains constant pressure in intracellular fluid and blood. Sodium chloride also increases the amount of fluid circulating in the vessels. The solution has such properties due to presence of sodium ions and chloride ions. They are capable of penetrating through the cell membrane using various transportation mechanisms, in particular, sodium-potassium pump. Sodium plays a significant role in signal transfer process in neurons. It is also involved in kidney metabolism and electrophysiological processes of human heart. In healthy state sufficient amounts of this compound is absorbed by the body with food products. But in the event of pathological changes, in particular, fluid loss (excessive sweating, vomiting etc.) there is increased discharge of these elements from the body. As a result, the body experiences a deficit of chloride and sodium ions. This also results in blood thickening and deterioration of nervous system and blood flow functions. The person experiences muscle cramps and spasms. Timely injection of isotonic sodium chloride solution into blood reinstates electrolyte balance [14].

But as passenger blood infusions are not possible during the fluids, oral taking of sodium chloride water solution together with other minerals (potassium chloride, sodium citrate, dextrose or glucose) may help improve osmotic concentration of blood and maintain electrolyte balance at sufficient levels.

Oral consumption of rehydration solutions containing all active substances (sodium citrate, sodium and potassium chloride, dextrose): REHYDRON®, HYDROVIT®, MARATONIK®, NORMOHYDRON®, ORASAN®, REOSOLAN®, HUMANA ELECTROLYTE® with osmotic concentration value of 26-280 mOsm/l, pH weakly alkaline—8.2 may be recommended to replenish water and electrolyte balance before and during the flight. Major goal of oral rehydration solution consumption is to reinstate or protect water-alkali balance; prevent blood pH and water-alkali balance disorders in the event of excessing sweating as a result of heat or physical stress. Glucose, one of main components of these solutions, helps maintain acid balance by means of absorption of salts and citrates. The osmotic concentration value of Rehydron solution is 260 mOsm/l, pH—8.2 and contains: NaCl—59.9 mmol, Na citrate—11.2 mmol, KCl—33.5 mmol, glucose—55.5 mmol, Na+—71.2 mmol, Cl+—93.5 mmol, K+—33.5 mmol, citrate—11.2 mmol. Compared to similar drugs REHYDRON® has a lower osmotic concentration value which is close to osmotic concentration value of blood plasma.

If REHYDRON® is taken for preventative purposes (in the event of excessive sweating) large amounts of water: 200 ml, 1 and 2 liters correspondingly have to be used for powder solution (18.9 g). REHYDRON® is taken in the amount that exceeds the loss of body weight caused by loss of fluid two-fold during the first 6-10 hours to replenish fluid loss. For example, if loss of body weight is 400 g, volume of REHYDRON® solution is 800 ml. No other liquids are required during this phase. It is also not recommended to eat during the first 4 hours of fluid replenishment.

To prevent dehydration the usual dose is 5-15 ml/kg of body weight: for children with body weight of less than 10 kg, the dose is 50-100 ml; adults and children with body weight of 10 kg and over, the dose is 100-200 ml [15]. 1 liter of boiled water is added into powder. The solution needs to be cooled and thoroughly mixed prior to consumption. The solution is taken in small sips. About 10 ml/kg of body weight needs to be consumed every hour. After the effect of dehydration is minimized, REHYDRON® dose is lowered to 50-10 ml/kg of patient body weight [15].

It was discovered that in line with pharmacological recommendations and calculated loss of fluid during flight (on average from 200 ml to 800 ml per hour) average passenger is recommended prior to boarding to dissolve one package (18.9 g) of one of oral rehydration solutions, for example, REHYDRON® in 1 liter of water and consume 0.5 liters, during next 2 hours of flight the remaining 0.5 liters of REHYDRON® has to be consumed. The dose for children with body weight of less than 10 kg is 50-100 ml. During the flight passengers have to avoid fatty food and food products with high content of simple sugars.

As such, due to the fact that blood thickens and blood transportation function deteriorates during the flight, we recommend to increase the osmotic concentration of blood in order to avoid blood thickening. Temporary increase of osmotic concentration of blood is achieved by consumption of oral rehydration solutions, for example, REHYDRON® powder. This increases osmotic concentration of blood plasma and blood remains thin for a certain period of time. The consumption of anticoagulants increases blood flow and will prevent thrombosis to avoid excessive coagulation during the flight.

Due to decreased atmospheric pressure and air expansion passengers experienced pain in confined spaces (stomach, sinuses etc.). In order to equalize pressure in the ears it is recommended to swallow saliva. To this end popsicles are given before the flight. It is not possible to equalize the pressure in the stomach. First, when small intestine is bloated, permeability of stomach walls changes and gases from the stomach flow into blood. This results in unhealthy sleepiness due to intoxicating impact of these gases. Second, small intestine bloating and lowered function of ileocecal valve result in small bowel bacterial overgrowth syndrome when microorganisms from large intestine travel to above departments of small intestine. This results in death of lactobifidumbacteria. SBBOS attributes to feeling of fatigue, headaches, anxiety, panic; predominantly low mood, dizziness, depressive state etc. In the event of serious deterioration of immune system bacteria may travel to lymph and blood with further inflammation with pus formation in all tissues and organs.

In order to prevent SBBOS (small bowel bacterial overgrowth syndrome) we recommend the following:
    take substances from foam preventative medicines with
        active component—simethicone. This group promotes
        adhesion of gas bubbles and foam destruction in the
        stomach (ESPUMISAN®, ESPUMISAN L®;
        METEOSPASMYL®; ANTIFLAT LANNAHER®;

SAB SIMPLEX®; SIMICOL®)—take some capsules before and during the flight [16];

as well as take prokinetics with active component domperidone, substances that improve intestinal motility (MOTILIUM®, DOMSTAL®, MOTORIKUM®, PERIDAL®, PERIDONE®);

take probiotics from several bottles that are natural substances and contain bacteria living in the stomach before the flight. These medicines are safe and do not cause any side effects. Medicines containing bifidum bacteria: BIFIDUMBACTERIN®, BIFIFORM®, LACTOBACTERIN®, BIOBACTON® etc. These microorganisms are the most common in human stomach. They are able to suppress pathogenic bacterial activity [17].

It was discovered and tested that as a result of such systematic impact on the body—increased osmotic concentration of blood, improved blood flow due to anticoagulants, prevention of small bowel bacterial overgrowth syndrome (BIFIDUMBACTERIA®, SIMETHICONE®, DOMPERIDONE®), we improve transportation function of blood (prevent strokes, heart attacks, thrombosis, thromboembolic) and maintain good immune system response. As a result of these systematic measures we obtain synergetic result: improved physical and emotional state, ability to think clearly throughout and after the flight.

The above description fully discloses the invention, including preferred scenarios of implementation. Modifications and improvement of implementation scenarios that have been described in detail in this statement are covered by invention formulae presented below. Without additional clarification we believe that the passenger can use this invention in full scope based on the above description.

DETAILED DESCRIPTION OF INVENTION

This invention is a way of synergetic minimization of negative impact of air flights on human health, including consumption of substances that improve osmotic concentration of blood plasma, in the form of oral rehydration solution, split into two intakes as a minimum, first intake in the amount of at least 0.3 liters up to 1 liter before boarding and further during the flight from half an hour to 2 hours at least 0.3 liters to 1 liter and on as-needed basis.

Oral rehydration solution, 1 sachet of REHYDRON® powder—18.9 g, containing sodium chloride—3.5 g, potassium chloride—2.5 g, sodium citrate—2.9 g and glucose—10 g with the following ratio: sodium chloride—18.5%, potassium chloride—13.2%, sodium citrate—15.3%, glucose—52.9% per 1 liter of water is used in one of scenarios of synergetic minimization of negative impact on flights on human body.

HYDROVIT® or MARATONIC® may also be used as oral rehydration solution instead of REHIDRON®.

One of additional measures for synergetic minimization of negative impact of flights on human body is a single dose of anticoagulant 20-30 minutes before the flight. Dissolvable ASPIRIN®, CARDIOMAGNYL®, WARFARIN® or HEPARIN® may be used as an anticoagulant.

One of additional measures for synergetic minimization of negative impact of flights on human body is prevention of small bowel bacterial overgrowth syndrome. To this end:

Bifidumbacteria probiotics are taken before boarding;
foam preventative substances with active simethicone component are taken in the amount of 4 capsules before boarding and another 4 capsules after the meal during the flight (1 capsule 40 mg each). ESPUMISAN® or ANTIFLAT®, SAB SIMPLEX® or SIMICOL® are used as foam preventative substances.

prokinetics with active domperidone component—2 pills before the flight and another 2 pills after the meal during the flight, 10 mg each, MOTILIUM®, DOMSTAL®, MOTORIKUM®, PERIDAL® or PERIDONE® or MOTILIUM® are used as prokinetics.

Case History

Case 1. Passenger Ilona L (31 years) experienced feet swelling, leg muscle cramps, fainting, had ear and stomach ache during Vienna-Moscow-Almaty flight. After the flight she had to be treated from small bowel bacterial overgrowth syndrome.

One month after during Almaty-Moscow-Vienna flight she took recommended substances in certain sequence and single doses: Rehydron solution in the amount of 0.5 l before boarding, and 0.5 l after 2 hours of flight, 1 pill of anticoagulant 20-30 minutes before the flight (1 dissolvable aspirin); 4 bottles of Bifidumbacterin probiotics before the flight, simethicone (ESPUMISAN®) 4 capsules before boarding and another 4 capsules after the meal during the flight (1 capsule 40 mg each), prokinetic with active ingredient domperidone (MOTILIUM®)—2 pills before the flight and another 2 pills after the meal during the flight, 10 mg each. The flight was easy, no feet swelling, no headache, ear ache was suppressed with a popsicle. She was feeling great after the flight.

Example 2. Passenger Yury B (71) experienced heart ache, leg pain, panic attack, had pain in the stomach and excessive sweating during Ust-Kamenogorsk—Moscow-San Francisco flight. He had heart stroke after landing and coronary artery stent placed in the US clinic. Three months after before boarding San Francisco-Moscow flight he took medicines for synergetic minimization of negative impact of the flight on health: intramuscular Cytochrome injections before the flight; Rehydron solution in the amount of 0.5 l before the flight and 0.5 l 2 hours after the flight; took the following before boarding: 4 bottles of Bifidumbacterin probiotics, 4 capsules of simethicone, prokinetic with active substance domperidone—2 pills; the following after the meal during the flight: simethicone—4 capsules (1 capsule 40 mg each) and 2 capsules of domperidone, 10 mg each. The flight was successful. There was no jet lag or fatigue feeling, no bloating and other negative consequences during the flight. He later successfully travelled to the clinic in Almaty City using means for synergetic minimization.

Multiple studies of synergetic minimization of negative impact of the flight on human health demonstrate that intake of above-mentioned substances and medicines with new pharmacological value in new conditions prevent feet swelling, bloating, jet lag and fatigue during the flight.

As such, the above-mentioned medicines with new pharmacological value (improved osmotic concentration of blood, prevention of small bowel bacterial overgrowth syndrome, improved immune system response) in new conditions are recommended to passengers in order to minimize negative impact of flights on human health in the following order:

to increase osmotic concentration of blood—1 sachet of oral rehydration solution—REHIDRON®, HYDROVIT® or MARATONIK®; take 0.5 l before the flight and another 0.5 2 hours after); to improve blood flow and prevent excessive coagulation take anticoagulants during the flight—dissolvable ASPIRIN® 1 tablet (20-30 minutes before the flight) or CARDIOMAGNYL® or WARFARIN® or HEPARIN® (Note. If passenger is already taking these substances, he does not need to take them additionally).

To prevent small bowel bacterial overgrowth syndrome:
- take probiotics, several bottles—Bifidumbacteria or Lactobacteria (before boarding).
- take foam preventive substances with active ingredient—simethicone, for example, ESPUMISAN® or METEOSPASMYL® or ANTIFLAT® or SAB SIMPLEX® or SIMICOL®)—4 capsules (before boarding and another 4 capsules after the meal during the flight);
- take prokinetics with active ingredient domperidone (MOTILIUM®, DOMSTAL®, MOTORIKUM®, PERIDAL®, PERIDON®), MOTILIUM®—2 tablets (before the flight and another 2 tables after the meal during the flight).

This invention promotes means of synergetic minimization of negative impact of the flight on passenger health with application of known substances and medicines with new pharmacological value in new conditions and attributes to positive state of health of passengers during the flight.

All methods used for synergetic minimization of negative impact of the flight on passenger health are known active substances with new pharmacological value in new conditions and are sold off-counter.

This range of known active pharmaceutical substances with new pharmacological value, including oral fixed dose, may be obtained by means of selection of the above-mentioned substances in therapeutic effective quantities with the standard kit:
- oral rehydration substances;
- anticoagulants;
- probiotics;
- foam preventative substances with active ingredient—simethicone;
- prokinetics with active ingredient domperidone.

This means of synergetic minimization of negative impact of the flights with consecutive consumption of the above active substances was tested in over 50 overseas flights during the past five years. We also perform studies of over 100 patients arriving into our clinic from abroad. Many patients state that they experienced panic, sleepiness, muscle cramps, small bowel bacterial overgrowth syndrome during the flight. They also suffered from sinusitis and vessel disorders (heart attack, stents placed) after the flights.

After utilization of declared means and instruction there was no panic, stomach aches, sleepiness, memory loss and mental confusion during the flight. Good boom was observed. The results were evaluated based on the following factors: complaints from passengers with regard to flight impact before and after utilization.

The studies were performed after the flight and then during the month after arrival through survey and visual examination. The obtained positive results were consistent during 2 months after the flights.

BIBLIOGRAPHY 1. http://avia-life.com., internet source Oct. 1, 2019.
2. https://nv.ua/opinion/recommends/kak-na-samom-dele-vlijajut-na-nas-aviaperelety-1996883.html, internet source Oct. 1, 2019.
3. D. V. Sivukhin. General physics.—M.: Fizmatlit, 2005.—T.P. Thermodynamics and molecular physics—21-22 pages—544 pages—ISBN 5-9221-0601-5; http://moykonspekt.ru/fizika/izotermicheskij-process-zakon-bojlya-mariotta/
4. Brief chemistry guide. Edition 4 (M, 1955, 113 pages); https://chem21.info/info/618833/
5. S. A. Ivanova. General Practitioner https://bebeku.ru/menyaetsya-arterialnoe-davlenie-samolete/, internet source Oct. 1, 2019.
6. Maya Milich https://aif.ru/health/life/22241,internet source Jan. 10, 2019
7. I. N. Bokarev, L. V. Popova. Study of application of low molecular heparine for treatment of deep vein thrombosis (Russian)//Difficult patients—2008—V 6, issue 10.—42 pages—48.—ISSN 2074-1995.
8. Air flight. Harmful health risks and means of minimization. Recommendations of doctor Bitterlich https://www.dokbit.com/puteshestviya-sovety-vracha/aviaperelet/255-meditsinskaya-bezopasnost-pri-aviaperelete, internet source Oct. 1, 2019.
9. https://alkomir.net/ponyatie-osmolyarnosti-plazmy-krovi-ee-normy-i-prichiny-narusheniya-standartnyh-pokazatelej-osmolyarnost-krovi-ponyatie-normy-v-analizah-o-chem-govoryat-izmeneniya-znachenij/, internet source Oct. 1, 2019.
10. https://alkomir.net/ponyatie-osmolyarnosti-plazmy-krovi-ee-normy-i-prichiny-narusheniya-standartnyh-pokazatelej-analiz-krovi-i-mochi-osmolyarnost/, internet source Oct. 1, 2019.
11. Yu. V. Natochin. Electrolytic homeostasis and its clinical value//Russian journal of anaesthesiology and intensive therapy—1999. —No 2.—33-52 pages.
12. W. J. Marshall. Clinical biochemistry—M.: BINOM, SP: Nevsky dialect, 1999.—367 pages.
13. N. I. Gubanov and A. A. Utepbergenov. Medical biophysics, 149 pages, M, 1978;
14. https://medside.ru/natriya-hlorid, internet source Oct. 1, 2019.
15. https://health.mail.ru/drug/rehydron/, internet source Oct. 1, 2019.
16. Yana Alexandrovna Tsygankova, medical observer, GP, high qualification category. https://okeydoc.ru/espumizan-instrukciya-po-primeneniyu-pokazaniya-i-protivopokazaniya/, internet source Oct. 1, 2019.
17. https://fb.ru/article/224899/mikroflora-kishechnika-vosstanovlenie-preparatyi-spisok-instruktsiya-po-primeneniyu-i-otzyivyi, internet source Oct. 1, 2019.

The invention claimed is:

1. A method of treating dehydration and restoring blood plasma osmolarity due to airline travel in a subject in need thereof, comprising administering to the subject an aqueous solution for oral rehydration, divided into at least two doses, the first dose in an amount of not less than 0.3 liters to 1 liter before boarding an airplane, and a second dose in the airplane in the time interval of after half an hour and up to 2 hours, in the amount of not less than 0.3 liters to 1 liter and as thirst occurs, and a therapeutically effective amount of an anticoagulant.

2. The method of claim 1, characterized in that 20-30 minutes before the air travel, a single dose of anticoagulant is taken, where the anticoagulant is effervescent acetylsalicyclic acid.

3. The method of claim 1, characterized in that 20-30 minutes before the air travel, a single dose of anticoagulant is taken, where the anticoagulant is acetylsalicyclic acid.

4. The method of claim 1, characterized in that 20-30 minutes before the air travel, a single dose of anticoagulant is taken, where the anticoagulant is warfarin.

5. The method of claim 1, characterized in that 20-30 minutes before the air travel, a single dose of anticoagulant is taken, where the anticoagulant is heparin.

6. The method of claim 1, characterized in that the oral rehydration solution is one dose or one sachet of of 18.9 g of powder containing 3.5 g sodium chloride, 2.5 g potassium chloride, 2.9 g sodium citrate, and 10 g glucose in the following ratio of components: 18.5% sodium chloride, 13.2% potassium chloride, 15.3% sodium citrate, and 52.9% glucose when dissolved in 1 liter of boiled water.

7. The method of claim 1, further comprising treating in the subject in need thereof small intestine bacterial overgrowth syndrome (SIBOS) caused by the airline travel by administering a therapeutically effective amount of (i) one or more probiotics or (ii) simethicone or simethicone and alvarine citrate or simethicone and dimethicone or (iii) a prokinetic medication.

8. The method of claim 1, characterized in that 20-30 minutes before the air travel, a single dose of anticoagulant is taken, where the anticoagulant is Rivaroxaban.

9. The method of claim 7, wherein the prokinetic medication is domperidone.

\* \* \* \* \*